United States Patent
Kara et al.

(10) Patent No.: US 9,926,239 B2
(45) Date of Patent: Mar. 27, 2018

(54) METHANATION PROCESS AND REACTOR FOR REACTING HYDROGEN WITH AT LEAST ONE CARBON-BASED COMPOUND AND PRODUCING METHANE AND WATER

(71) Applicant: GDF SUEZ, Courbevoie (FR)

(72) Inventors: Ylmaz Kara, Eaubonne (FR); Bernard Marchand, Paris (FR)

(73) Assignee: GDF SUEZ, Courbevoie (FR)

( * ) Notice: Subject to any disclaimer, the term of this patent is extended or adjusted under 35 U.S.C. 154(b) by 0 days.

(21) Appl. No.: 15/024,831

(22) PCT Filed: Sep. 25, 2014

(86) PCT No.: PCT/FR2014/052411
§ 371 (c)(1),
(2) Date: Mar. 24, 2016

(87) PCT Pub. No.: WO2015/044601
PCT Pub. Date: Apr. 2, 2015

(65) Prior Publication Data
US 2016/0236999 A1     Aug. 18, 2016

(30) Foreign Application Priority Data
Sep. 26, 2013   (FR) ..................................... 13 59313

(51) Int. Cl.
C07C 1/04       (2006.01)
C10L 3/08       (2006.01)

(52) U.S. Cl.
CPC .............. *C07C 1/0415* (2013.01); *C07C 1/04* (2013.01); *C07C 1/041* (2013.01); *C07C 1/042* (2013.01);
(Continued)

(58) Field of Classification Search
CPC ....... C07C 1/041; C07C 1/0415; C07C 1/048; C10L 3/08; B01J 2208/00362; B01J 2208/00902; B01J 2219/00247
See application file for complete search history.

(56) References Cited

U.S. PATENT DOCUMENTS 3,991,096 A * 11/1976 Bortolini ................ B01J 8/1809
                                                                 558/320
4,312,741 A    1/1982 Jacquin
(Continued)

FOREIGN PATENT DOCUMENTS

DE       25 06 199 A1    11/1975
WO       2012/035881 A1   3/2012

OTHER PUBLICATIONS

Patent No. DE2506199, Nov 13, 1975, pp. 1-3; English translation.*
Helmeth ("Methanation process" Dec. 13, 2014, pp. 1-4).*

*Primary Examiner* — Medhanit W Bahta
(74) *Attorney, Agent, or Firm* — PatShegen IP

(57) ABSTRACT

A methanation reactor for reacting dihydrogen with a carbon-based compound and producing methane. The reactor has a hollow body configured to receive a fluidized bed of catalytic particles, an inlet for each carbon-based compound and dihydrogen, and an outlet for methane and water. A water inlet is provided to inject liquid-phase cooling water into the fluidized bed. When each carbon-based compound is a gas, the reactor has at least one water-injection nozzle and at least one gas injection nozzle for a gas consisting of the carbon-based gas and dihydrogen, and at least one water-injection nozzle positioned below the gas-injection nozzle. The flow rate of water introduced into the hollow body can depend on the temperature measured in the reactor.

11 Claims, 2 Drawing Sheets

(52) U.S. Cl.
CPC ............... *C07C 1/048* (2013.01); *C10L 3/08* (2013.01); *B01J 2208/00362* (2013.01); *B01J 2208/00902* (2013.01); *B01J 2219/00247* (2013.01); *C07C 1/0405* (2013.01)

(56) References Cited

U.S. PATENT DOCUMENTS

| | | | | |
|---|---|---|---|---|
| 4,359,448 | A | * | 11/1982 | Schuurman ............ B01J 8/1836 165/104.16 |
| 4,431,751 | A | * | 2/1984 | Hohlein .................... C07C 1/02 122/4 D |
| 4,839,391 | A | * | 6/1989 | Range .................... B01J 8/0285 518/712 |
| 2012/0178833 | A1 | * | 7/2012 | Clomburg, Jr. ......... C07C 1/041 518/711 |
| 2013/0041051 | A1 | * | 2/2013 | Zuberbuhler ............ B01J 8/001 518/712 |

\* cited by examiner

METHANATION PROCESS AND REACTOR FOR REACTING HYDROGEN WITH AT LEAST ONE CARBON-BASED COMPOUND AND PRODUCING METHANE AND WATER

RELATED APPLICATIONS

This application is a § 371 application from PCT/FR2014/052411 filed Sep. 25, 2014, which claims priority from French Patent Application No. 13 59313 filed Sep. 26, 2013, each of which is herein incorporated by reference in its entirety.

TECHNICAL FIELD OF THE INVENTION

The present invention relates to a methanation reactor for reacting hydrogen with a carbon-based compound and producing methane. It applies in particular to industrial methanation and the co-generation of thermal energy and methane.

STATE OF THE ART

Methanation is an industrial process that catalytically converts hydrogen and carbon monoxide or carbon dioxide into methane.

The formula for the methanation reaction varies according to the nature of the carbon-based compound. Depending on the case, this formula is:

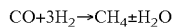

$$CO+3H_2 \rightarrow CH_4 \pm H_2O$$

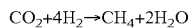

$$CO_2+4H_2 \rightarrow CH_4+2H_2O$$

In order to optimize the yields of this reaction, a catalyst bed is placed in a reactor in which the reaction occurs. This bed can be fixed or fluidized. As the methanation reaction is highly exothermic, it gives rise to significant requirements to remove heat, and therefore to cool the reactor. A fluidized catalyst bed allows the temperature of the reactive area to be homogenized. Lastly, the kinetics of this reaction at the temperatures normally utilized are high, requiring as a consequence a small amount of catalyst.

In current fixed-bed systems, known as "Throughwall Cooled Reactors", a heat transfer is produced by reactor walls cooled by a coolant fluid. However, significant surface areas are required to produce the heat transfer and the costs of manufacturing the reactor are high.

In current fluidized-bed systems, one or more heat exchangers are immersed in the fluidized bed inside the reactor. Then, for example, water, water vapor or a thermal oil are circulated in these exchangers. The thermal exchange coefficients between the wall of the exchanger and the fluidized bed are very high, of the order of thermal exchange coefficients between a liquid and a wall. However, the use of thermal oils is only possible up to reaction temperatures of the order of 380° C. to 400° C. In addition, in these systems the size of the reactor depends upon the size occupied by each exchanger to be immersed in the fluidized bed. These systems lead to manufacturing costs and a non-optimized use of space for the reactor. In addition, the efficiency of the heat exchanges between the bed and the coolant fluid are highly dependent upon the fluidization conditions.

In current fixed-bed or fluidized-bed systems, the injection of vapor mixed with hydrogen and the carbon-based compound makes it possible to limit the formation of a carbon deposit in the form of coke on the catalyst, one of the consequences of which is the premature deactivation of the catalyst. Lastly, as methanation catalysts are preferably made at least in part of nickel, the methanation reaction risks leading to the formation of carbonyl, a highly toxic compound, on contact with walls brought to a temperature of less than 260° C., which makes the cooling system more complex.

Documents WO2012/035881, U.S. Pat. No. 4,312,741 and DE2506199 are known. The teachings of these documents do not make it possible to achieve cooling of a methanation reactor while limiting the formation of coke or carbonyl in the reactor.

In particular, document WO2012/035881 describes a reactor with inlets and outlets that can implement a methanation reaction. However, this reactor does not comprise an inlet for injecting water into the reactor to cool down the chemical reaction.

Document U.S. Pat. No. 4,312,741 describes a methanation reactor. However, this reactor does not comprise a liquid-phase water inlet into the reactor.

Document DE2506199 describes a methanation reactor with a water inlet above a catalyst bed contained in the reactor. This system has the drawback of not limiting the formation of coke or carbonyl in the reactor during the injection of water.

SUBJECT OF THE INVENTION

The present invention aims to remedy all or part of these drawbacks.

To this end the present invention envisages, according to a first aspect, a methanation reactor for reacting dihydrogen with at least one carbon-based compound and producing methane, comprising:

a hollow body configured to receive a fluidized bed of catalytic particles and comprising an inlet for each carbon-based compound and for dihydrogen and an outlet for methane and water, and which also comprises an inlet for the injection of liquid-phase cooling water into the fluidized bed.

Although introducing a product of the reaction, in addition to reagents, into the fluidized bed of the reactor is, in principle, the opposite of what the person skilled in the art does to obtain a good yield from the reaction, the inventors have determined that this introduction is favorable in terms of controlling the temperature inside the reactor, the reactor's dimensions, the reactor's complexity, and the manufacturing and maintenance costs of the reactor, insofar as the reagent is introduced in liquid phase. This introduction also makes it possible to reduce, even eliminate, the production of carbonyl. Lastly, this introduction allows the formation of coke on the surface of the catalyst surface to be limited; the injected water is vaporized on contact with the hot bed.

Thanks to the characteristics of the reactor that is the subject of the present invention, the reactor's size can be defined as a function of the quantity of catalytic bed to be contained to convert the hydrogen and the carbon-based compound. In addition, the water introduced is used by the methanation reaction through the "Water Gas Shift" reaction, in which carbon monoxide and water produce carbon dioxide and dihydrogen. Lastly, these provisions make it possible to obtain, on output from the reactor, a water molar composition of the water vapor and methane mixture that is higher than 50%.

In certain embodiments, the input of each carbon-based compound and the dihydrogen is realized in the bed.

These embodiments make it possible to increase the yields of the reaction between each carbon-based compound and the dihydrogen in the catalyst. The input of water in the bed means it can be cooled without risk of carbonyls forming on contact with the walls.

In certain embodiments, the water inlet is closer to the base of the hollow body than the inlets of each carbon-based compound and of the dihydrogen.

These embodiments make it possible to prevent the deposit of coke on the catalyst.

In certain embodiments, each carbon-based compound is a gas, the reactor comprising at least one water-injection nozzle and at least one injection nozzle for a gas comprising the carbon-based gas and dihydrogen, at least one water-injection nozzle being positioned below at least one gas-injection nozzle.

These embodiments allow an optimized injection of gas and water into the hollow body of the reactor.

In certain embodiments, the reactor that is the subject of the present invention comprises a means of condensing water vapor present downstream of the outlet for methane and water.

These embodiments allow the water to be separated, by condensation, from the methane downstream of the methane outlet. In addition, these embodiments allow the condensed water to be recovered.

In certain embodiments, the reactor that is the subject of the present invention comprises a circuit for transporting condensed water to the inlet for injecting cooling water.

These embodiments make it possible to recycle the water created by the methanation reaction for cooling this reaction.

In certain embodiments, the reactor that is the subject of the present invention comprises, downstream of the outlet for methane and water, a gas-solid separation means.

These embodiments make it possible to ensure that the methane and water output from the device are in gas phase and to prevent the presence of solids on output from the device such as, for example, particles from the catalyst bed.

In certain embodiments, the reactor that is the subject of the present invention comprises a temperature sensor in the reactor and a means of regulating the flow rate of the water introduced into the hollow body as a function of the temperature measured by the temperature sensor.

These embodiments allow the reaction temperature to be optimized so as to obtain an optimum yield of methane according to the carbon-based compound introduced into the reactor.

In certain embodiments, the reactor that is the subject of the present invention comprises a heat exchanger, downstream of the outlet for methane and water, configured to cool the methane and water and to co-generate thermal energy during the heat exchange realized.

These embodiments make it possible to co-generate thermal energy and methane, from the water vapor and methane mixture on output from the hollow body.

In certain embodiments, the amount of water introduced into the hollow body by the water injection inlet is more than 75% of the amount of water output from the hollow body. The water introduced therefore results in an especially high level of cooling.

According to a second aspect, the present invention envisages a methanation method for reacting dihydrogen with at least one carbon-based compound and producing methane, comprising:

a step of inputting each carbon-based compound and dihydrogen into a hollow body configured to receive a fluidized bed of catalytic particles, a step of methanation reaction between the hydrogen and each carbon-based compound, and p a step of outputting methane and water;

and which also comprises a step of injecting liquid-phase cooling water into the fluidized bed during the methanation reaction step.

As the particular features, advantages and aims of this method are similar to those of the methanation reactor that is the subject of the present invention, they are not repeated here.

BRIEF DESCRIPTION OF THE FIGURES

Other particular advantages, aims and features of the invention will become apparent from the non-limiting description that follows of at least one particular embodiment of the methanation reactor and the methanation method that are the subjects of the present invention, with reference to drawings included in an appendix, wherein.

DESCRIPTION OF EXAMPLES OF REALIZATION OF THE INVENTION

The present description is given as a non-limiting example.

Figure 1:
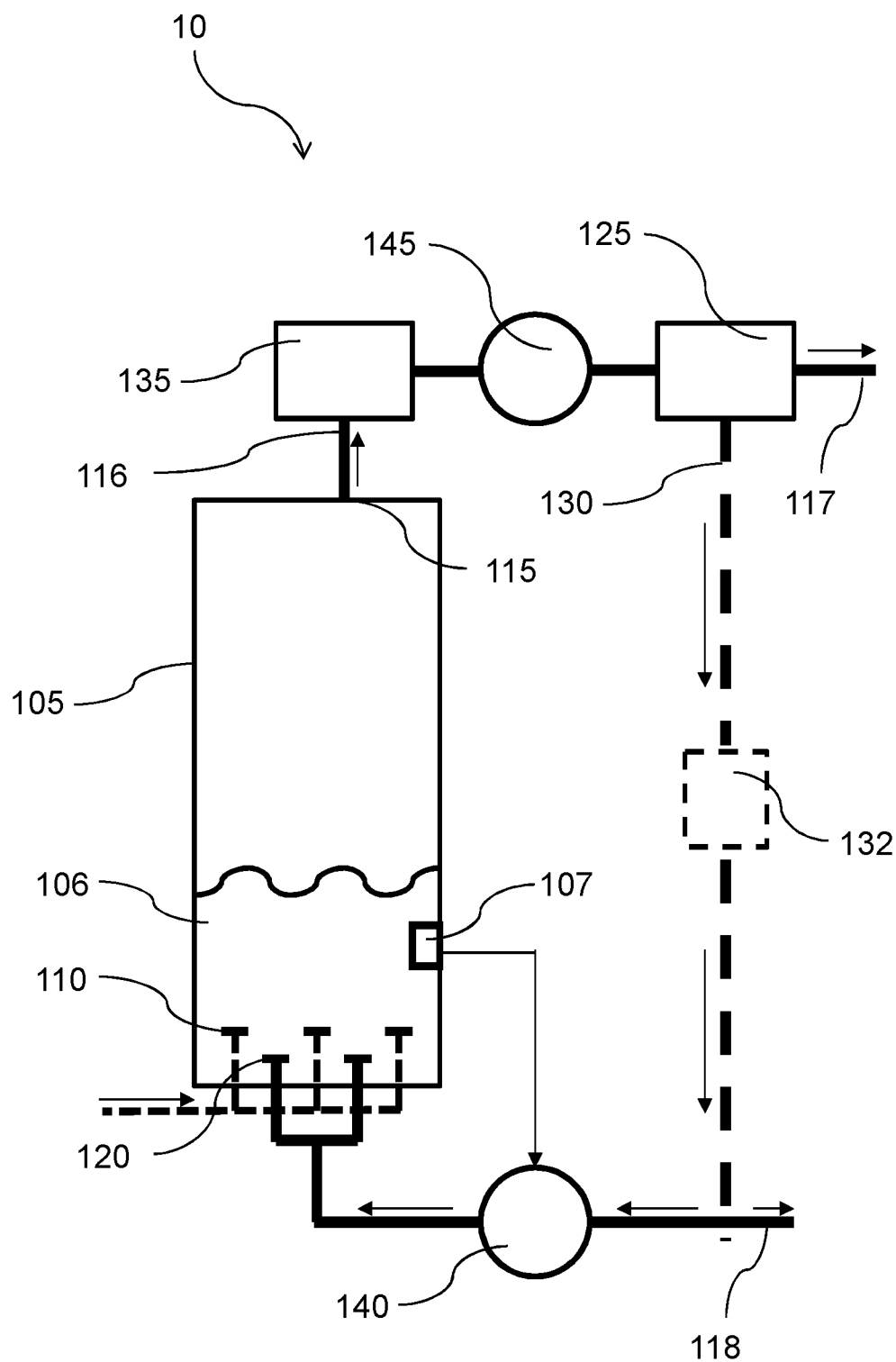
FIG. 1 represents, schematically, a particular embodiment of the methanation reactor that is the subject of this invention.

It is now noted that FIG. 1 is not to scale.

FIG. 1 shows a first particular embodiment of the reactor 10 that is the subject of the present invention. This reactor 10 comprises:

a hollow body 105 configured to receive a fluidized bed of catalytic particles 106 and which comprises at least one nozzle 110 for injecting a carbon-based compound and dihydrogen, and at least one nozzle 120 for injecting water;

an outlet 115 for methane and water;

a means of gas-solid separation 135 for the methane produced by the methanation reaction;

a heat exchanger 145 configured to cool the methane and water and to co-generate thermal energy during the heat exchange realized;

a means of condensing 125 water vapor present downstream of the methane outlet 115;

a circuit 130 for transporting condensed water to a nozzle for injecting cooling water 120; and a means of regulating 140 the flow rate of the water introduced into the hollow body 105 as a function of the temperature measured in the reactor 10 by a temperature sensor 107.

The hollow body 105 is, for example, a metallic cylinder of revolution closed at its extremities. This hollow body 105 is partially filled with a fluidized catalyst bed. Through the action of gravity, this catalyst is located near the base of the hollow body 105. This hollow body 105 comprises at least one carbon-based compound and dihydrogen injection nozzle 110, allowing the carbon-based compound and dihydrogen to be introduced into the fluidized bed. Preferably, the carbon-based compound is carbon monoxide or carbon dioxide in gaseous form.

In addition, the hollow body 105 comprises at least one nozzle 120 for injecting cooling water. The outlet of each nozzle 120 for injecting cooling water is preferably closer to the base of the hollow body 105 than the outlet of each nozzle 110 for injecting the carbon-based compound. In this way, the injected water is very quickly brought to the vapor state on contact with the fluidized bed, absorbing phase-change latent heat.

As most of the heat exchange between the injected water and the fluidized bed occurs in the vicinity of the cooling water injection nozzle 120, the temperature of the fluidized bed at the location of the carbon-based compound injection nozzle 110 is higher than 260° C., which reduces or even eliminates the formation of carbonyl.

Preferably, the amount of water introduced by the water injection nozzles 120 is more than 75% of the amount of water output from the hollow body, more preferably more than 80% and, even more preferably, more than 85%. The injection of water, by the injection nozzles 120, is preferably realized directly into the fluidized bed contained in the hollow body 105.

This hollow body 105 comprises, lastly, a methane and water vapor outlet 115 that emerges onto a duct 116. This duct takes the methane and water vapor to a means of gas-solid separation 135 for the methane output. This gas-solid separation means 135 is, for example, a filter configured to hold the fine catalyst particles that may be transported by the methane and/or the water vapor.

This reactor 10 also comprises, downstream of the gas-solid separation means 135, a heat exchanger 145 configured to cool the methane and water and to co-generate thermal energy during the heat exchange realized. This exchanger 145 is, for example, a U-shaped tube heat exchanger. In some variants, this exchanger 145 is an exchanger from amongst the following:
horizontal tube bundle heat exchanger;
vertical tube bundle heat exchanger;
spiral heat exchanger;
plate heat exchanger;
block heat exchanger; or
finned heat exchanger.

This reactor 10 also comprises, downstream of the heat exchanger 145, a means of condensing 125 water vapor. This condensation means 125 is, for example, a condenser with separated fluids. In some variants, this condensation means 125 is a condenser with direct contact between a coolant fluid and the vapor to be condensed. In other variants, this condensation means 125 is a shell-and-tube or tube bundle heat exchanger. In these variants, the heat exchanger 145 and the condensation means 125 are combined into a single device. The methane, not condensed, exits via a duct 117.

In some variants, downstream of the condensation means 125, the reactor 10 comprises the circuit 130 for transporting condensed water, one part of which is evacuated by an output duct 118 and one part of which is transported to the nozzles 120 for injecting cooling water by utilizing a pump 132. The proportion of water recycled in this way is of the same order of magnitude as the condensate flow-rate, i.e. of the order of 85% to 95% depending on the temperature of the condensation means.

The reactor 10 also comprises a means of regulating 140 the flow rate of the water introduced into the hollow body 105 as a function of the temperature measured in the bed in the reactor 10 by a temperature sensor 107. The regulation means 140 is, for example, a valve controlled pneumatically or electronically by an electronic circuit (not shown). This electronic circuit receives information representative of the temperature inside the hollow body 105 and actuates the valve as a function of the information received so that the flow-rate of water introduced into the hollow body is an increasing function of the temperature measured. In this way a control loop is realized for the interior temperature in the fluidized catalyst bed of the hollow body 105.

Figure 2:
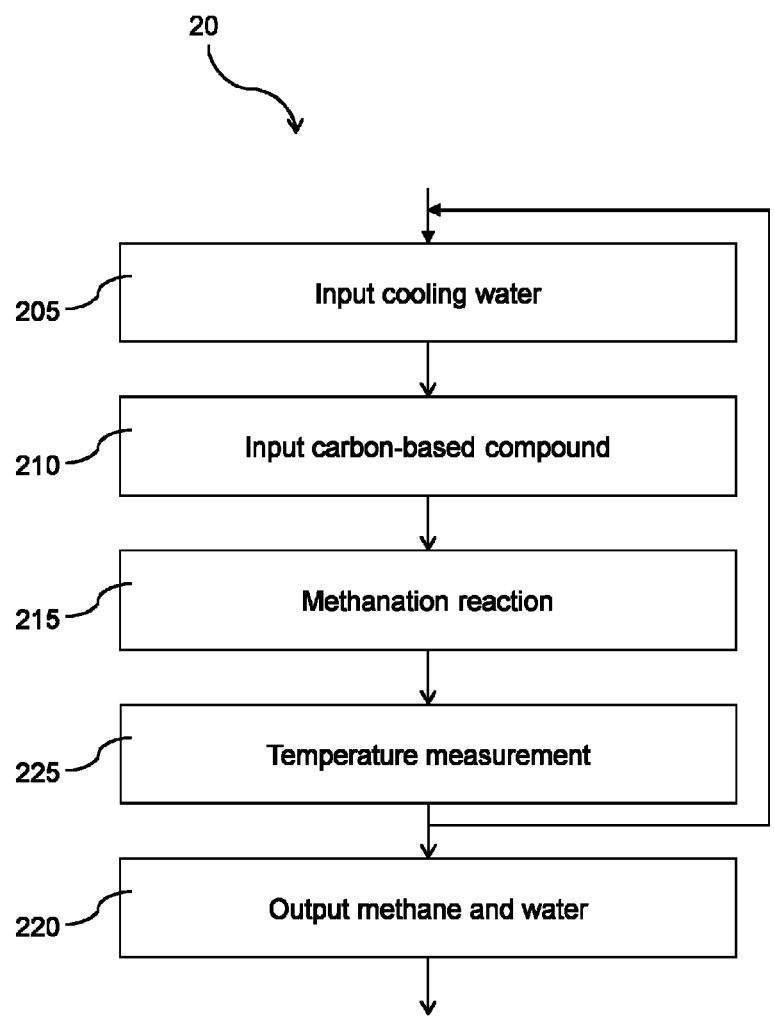
FIG. 2 represents, in the form of a logical diagram, steps in a particular embodiment of the methanation method that is the subject of the present invention.

FIG. 2 shows logical diagram of steps in a particular embodiment of the methanation method 20 that is the subject of the present invention. The method 20 comprises:
a step 205 of injecting liquid-phase cooling water into a fluidized bed contained in a hollow body during a methanation reaction step 215;
a step 210 of inputting the carbon-based compound and hydrogen into the hollow body configured to receive a fluidized bed of catalytic particles;
a step 215 of methanation reaction between the hydrogen and the carbon-based compound to produce methane and water;
a step 225 of measuring the temperature inside the hollow body; and
a step 220 of outputting methane and water.

The step 205 of injecting cooling water into the hollow body is realized, for example, by utilizing cooling water injection nozzles that inject the water at the location of a fluidized catalyst bed contained in the hollow body.

The step 210 of inputting the carbon-based compound and hydrogen into the hollow body is realized, for example, by utilizing cooling water injection nozzles for injecting carbon monoxide or dioxide and dihydrogen. These injection nozzles inject the gas above at least one, and preferable all, of the cooling water injection nozzles.

The step 220 of outputting methane and water is realized, for example, by utilizing a duct, one inlet of which is located on an upper portion of the hollow body.

The measurement of the temperature inside the hollow body carried out during the step 225 is used to slave the flow-rate of the water introduced into the hollow body during the step 205, this flow-rate being an increasing function of the temperature inside the hollow body.

The various steps shown in FIG. 2 are performed continuously and simultaneously during the nominal operation of the reactor. Preferably, the water introduced into the hollow body during the step 205 is the water from the reaction cooled by a condenser and, possibly, a heat exchanger, or a device combining the functions of a condenser and a heat exchanger.

As can be seen by reading the description above, the present invention enables the size of a methanation reactor to be reduced. In effect the injection of water directly into the reaction medium means that one does not have to use a heat exchanger wherein the exchange surfaces to be used are large. In addition, the injected water is used within the reactor through the gas to water reaction formula so as to ensure the presence of dihydrogen in the methanation reaction. In addition, the presence of a water condensation means downstream of the methane and water outlet allows the water produced naturally by the methanation reaction to be recycled for subsequently cooling the reaction. Lastly, the temperature inside the reactor is slaved by introducing water according to an increasing function of the temperature measured in the reactor, and the production of carbonyl can be minimized.

The invention claimed is:

1. A methanation method for reacting dihydrogen with at least one of carbon monoxide and carbon dioxide in a gaseous form and producing a methane, comprising the steps of:
providing inside a hollow body of methanation reactor a fluidized bed of catalytic particles;
injecting a liquid-phase cooling water into a first location of said fluidized bed for mixing the liquid-phase cooling water with the catalytic particles such that the liquid-phase cooling water vaporizes on contact with the fluidized bed in said first location, absorbing thereby phase-change latent heat;

inputting said at least one of carbon monoxide and carbon dioxide and dihydrogen into a second location inside said fluidized bed, said second location having said vaporized cooling water allowing thereby methanation reaction between said at least one of carbon monoxide and carbon dioxide and hydrogen; and outputting the methane and water produced from the methanation reaction;

wherein said second location is distanced from said first location such that temperature of said at least one of carbon monoxide and carbon dioxide in said second location is configured to minimize coke deposit formation and while cooling the methanation reaction.

2. The methanation method according to claim 1, wherein said at least one of carbon monoxide and carbon dioxide and the dihydrogen is input in the fluidized bed.

3. The methanation method according to claim 2, wherein said first location is closer to a base of the hollow body than said second location.

4. The methanation method according to claim 3, wherein the step of injecting being achieved by at least one water-injection nozzle and the step of inputting being achieved by at least one gas injection nozzle to inject a gas comprising said at least one of carbon monoxide and carbon dioxide gas and dihydrogen, said at least one water-injection nozzle being positioned below said at least one gas-injection nozzle.

5. The methanation reactor according to claim 2, wherein the step of injecting being achieved by at least one water-injection nozzle and the step of inputting being achieved by at least one gas injection nozzle for a gas comprising said at least one of carbon monoxide and carbon dioxide gas and dihydrogen, said at least one water-injection nozzle being positioned below said at least one gas-injection nozzle.

6. The methanation method according to claim 1, further comprising a step of condensing water vapor present downstream of the step of outputting of methane and water.

7. The methanation method according to claim 6, further comprising a step of transportation of the condensed water to the water injection step.

8. The methanation method according to claim 1, further comprising, downstream of the step of outputting methane and water, a gas-solid separation step.

9. The methanation method according to claim 1, further comprising a step of temperature sensing in the reactor and a step of regulation of a flow rate of the liquid-phase cooling water introduced into the hollow body as a function of the temperature measured by the temperature sensing step.

10. The methanation method according to claim 1, further comprising a heat exchange step, downstream of the step of outputting methane and water, to cool the methane and water and to co-generate a thermal energy during the heat exchange.

11. The methanation method according to claim 1, wherein the amount of the liquid-phase cooling water introduced into the hollow body by the water inlet is more than 75% of the amount of the water output from the hollow body.

* * * * *